United States Patent [19]
Ogawa

[11] Patent Number: 5,414,367
[45] Date of Patent: May 9, 1995

[54] APPARATUS FOR DETECTING ALCOHOL CONCENTRATION IN A MIXED FUEL

[75] Inventor: Kenji Ogawa, Himeji, Japan

[73] Assignee: Mitsubishi Denki Kabushiki Kaisha, Tokyo, Japan

[21] Appl. No.: 209,102

[22] Filed: Mar. 11, 1994

[30] Foreign Application Priority Data

Mar. 15, 1993 [JP] Japan ................. 5-054105

[51] Int. Cl.⁶ ............. G01R 27/26; G01N 27/00
[52] U.S. Cl. ..................... 324/663; 331/65; 73/61.44; 324/682
[58] Field of Search ............ 324/663, 681, 682, 685, 324/667, 668; 73/61.43, 61.44; 331/65

[56] References Cited

U.S. PATENT DOCUMENTS

| | | | |
|---|---|---|---|
| 4,112,744 | 9/1978 | Tassano | 324/685 |
| 4,187,462 | 2/1980 | Haker et al. | 324/682 |
| 4,468,611 | 8/1984 | Tward | 324/685 |
| 4,470,300 | 9/1984 | Kobayashi | 324/681 |
| 5,091,704 | 2/1992 | Kopera | 324/682 |
| 5,134,381 | 7/1992 | Schmitz et al. | 324/685 |
| 5,261,276 | 11/1993 | Gonze et al. | 324/685 |
| 5,313,168 | 5/1994 | Ogawa | 324/682 |

FOREIGN PATENT DOCUMENTS

| | | | |
|---|---|---|---|
| 0217495 | 4/1987 | European Pat. Off. | 324/685 |
| 534310 | 2/1993 | Japan . | |
| 5-093703 | 4/1993 | Japan | 324/685 |
| 5-099879 | 4/1993 | Japan | 324/685 |

Primary Examiner—Maura K. Regan
Attorney, Agent, or Firm—Sughrue, Mion, Zinn, Macpeak & Seas

[57] ABSTRACT

An apparatus for detecting the concentration of alcohol mixed with gasoline or light oil comprises a dielectric constant detection device for providing a resonance frequency corresponding to the dielectric constant of the mixed fuel; a device for detecting the resonance frequency provided by the dielectric constant detection device so as to output a first frequency signal having the same frequency as the resonance frequency; a frequency divider which divides the first frequency signal by a variable factor; a fuel temperature detector which outputs a second frequency signal representing the detected temperature; and a dividing factor decision device for determining the frequency dividing factor based on the first and second frequency signals. The alcohol concentration is determined by the output frequency of the frequency divider.

4 Claims, 8 Drawing Sheets

FIG. 11 PRIOR ART

APPARATUS FOR DETECTING ALCOHOL CONCENTRATION IN A MIXED FUEL

BACKGROUND OF THE INVENTION

1. Field of the Invention

The present invention relates to an apparatus for detecting the concentration of alcohol contained in liquid such as fuel supplied to a combustor or the like. More particularly, the present invention relates to an apparatus for detecting the concentration of alcohol contained in alcohol-mixed fuel used for an automotive internal combustion engine.

2. Description of the Related Art

In recent years, the U.S. and various countries in Europe have been tried to use mixed fuel in which gasoline is mixed with alcohol such as methanol as automotive fuel in order to reduce the consumption of oil and to reduce the air pollution. However, if alcohol-mixed fuel is directly used in an engine which is tuned to match an air-fuel ratio of gasoline, then difficulties with engine operation will occur due to a lean air-fuel ratio which results from the fact that the theoretical air-fuel ratio of alcohol is lower than that of gasoline. Therefore, it is required to detect the alcohol content or the concentration of alcohol contained in the alcohol-mixed fuel so as to adjust the air-fuel ratio and the ignition timing according to the detected value of the alcohol concentration.

In known techniques, the alcohol content is determined by detecting either the dielectric constant or the refractive index of alcohol-mixed fuel. One method of detecting the dielectric constant is disclosed in Japanese Patent Laid-Open No.4-262249, which will be described below, referring to the figures.

Figure 8:
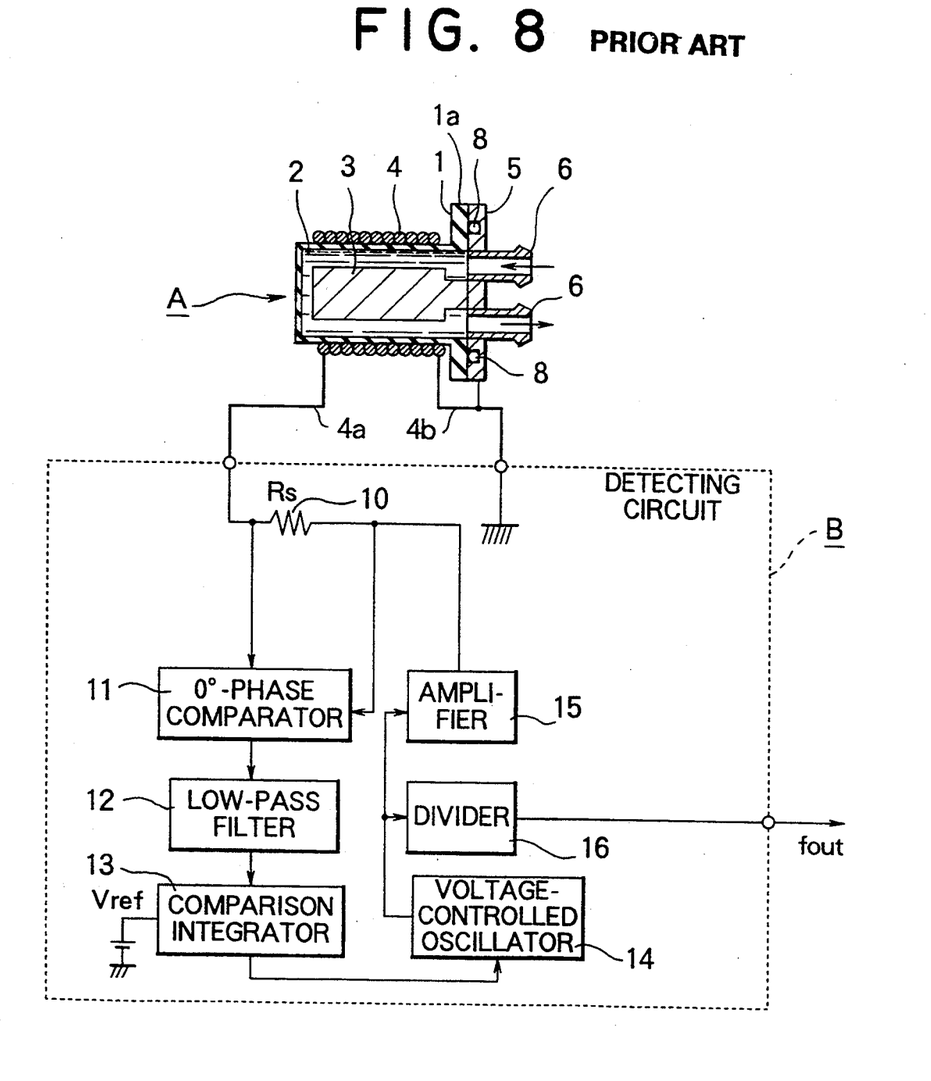
FIG. 8 is a block diagram illustrating a conventional apparatus for detecting the alcohol concentration of fuel.
Figure 9:
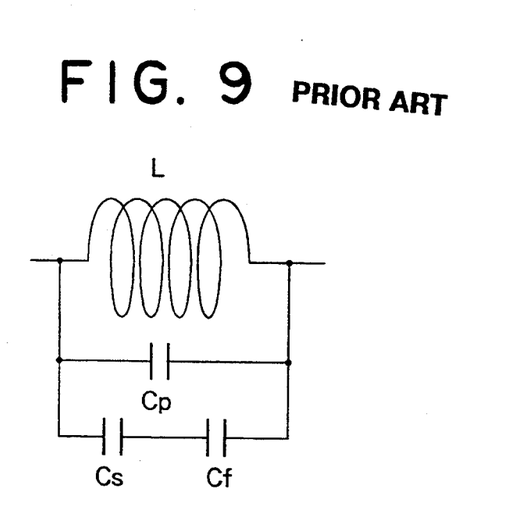
FIG. 9 is a circuit diagram illustrating an equivalent circuit of a sensor A in FIG. 8.

FIG. 8 is a block diagram illustrating a conventional apparatus for detecting the alcohol concentration of alcohol-mixed fuel containing alcohol such as methanol, according to the method disclosed in Japanese Patent Laid-Open No.4-262249. As shown in FIG. 8, the conventional apparatus for detecting the alcohol concentration comprises a sensor A and a detecting circuit B. The sensor A comprises an LC parallel resonant circuit which provides a resonant frequency f corresponding to the dielectric constant $\epsilon$ of alcohol-mixed fuel. FIG. 9 shows a simplified equivalent circuit of this LC parallel resonant circuit, which will be described in more detail later. The sensor A includes a barrel-shaped insulating tube 1 made of an insulating material such as ceramic or oil-resistant plastic. The barrel-shaped insulating tube 1 is provided with a rim 1a extending outward from an open end of the insulating tube 1. The sensor A also includes an electrically-conductive electrode 3 having a cylindrical shape coaxial to the barrel-shaped insulating tube 1 wherein the conductive electrode 3 is disposed in the barrel-shaped insulating tube 1 such that the conductive electrode 3 is substantially parallel to the barrel-shaped insulating tube 1. The sensor A also includes a single-layer winding coil 4 wound around the outside of the barrel-shaped insulating tube 1 such that the coil 4 is opposed to the conductive electrode 3 which is disposed within the barrel-shaped insulating tube 1. Both ends of the single-layer winding coil 4 are electrically connected to leads 4a and 4b, respectively, as shown in FIG. 8. As shown in FIG. 8, the lead 4a is connected to one end of a resistor Rs (10) provided in the detecting circuit B, which will be described in more detail later. The lead 4b is grounded in the detecting circuit B. A fuel path 2 is formed between the outer surface of the conductive electrode 3 and the inner surface of the single-layer winding coil 4 via the wall of the barrel-shaped insulating tube 1 so that fuel to be detected can flow through the fuel path 2. The conductive electrode 3 is also provided with a flange 5. The flange 5 is fixed via a fuel seal 8 to the rim 1a of the barrel-shaped insulating tube 1. The flange 5 may be formed as an integral part of the conductive electrode 3. A fuel chamber is formed with these elements described above. A pair of nipples 6 are provided through the flange 5 so that the fuel may be introduced into the fuel path 2.

The detecting circuit B for detecting the resonant frequency f provided by the sensor A will be described below. The detecting circuit B comprises: a resistor Rs (10) which is electrically connected to the lead 4a of the single-layer winding coil 4 in such a manner that a series circuit is formed to be composed of the resistor Rs (10) and the single-layer winding coil 4; a zero-degree phase comparator 11 for making comparison in phase between the voltage signals appearing at each end of the resistor 10; a low-pass filter 12 electrically connected to the zero-degree phase comparator 11 for smoothing the output of the zero-degree phase comparator 11 so as to provide a DC voltage corresponding to the difference in phase between the above-described voltage signals; a comparison integrator 13 which makes comparison between the DC voltages provided from the low-pass filter 12 and a predetermined reference voltage Vref corresponding to the phase of 0° so as to provide an output signal representing the integration of the differences obtained by the comparison; a voltage-controlled oscillator 14 electrically connected to the comparison integrator 13 for providing an oscillating voltage having an oscillation frequency corresponding to the output of the comparison integrator 13; a frequency divider 16 electrically connected to the voltage-controlled oscillator 14 for providing a signal fout to the outside circuit wherein the signal fout is obtained by dividing the output frequency of the oscillating signal provided by the voltage-controlled oscillator 14; and an amplifier 15 electrically connected to the voltage-controlled oscillator 14 for amplifying the oscillating output provided by the voltage-controlled oscillator 14 so as to apply the amplified output to the series circuit comprising the resistor 10 and the single-layer winding coil 4.

Now, the operation of the conventional alcohol concentration detector will be described below. As described above, the sensor A, shown in FIG. 8, comprises an LC parallel resonant circuit which can be substantially represented by an equivalent circuit shown in FIG. 9, where L is the inductance of the single-layer winding coil 4, Cf is the capacitance distributed between the single-layer winding coil 4 and the conductive electrode 3 wherein the capacitance Cf varies depending on the dielectric constant $\epsilon$ of the fuel passing through the fuel path 2, Cs is the capacitance associated with a dielectric or an insulating material included in the barrel-shaped insulating tube 1 which protects the single-layer winding coil 4 from the fuel, and Cp is the total stray capacitance associated with the lead 4a of the single-layer winding coil 4 and the input capacitance of the zero-degree phase comparator 11 and the like wherein the capacitance Cp is independent of the dielectric constant $\epsilon$ of the fuel.

If the varying frequency of the output signal, which is applied by the amplifier 15 to the lead 4a of the sensor A, is varied, the sensor A exhibits an LC parallel resonance state. The parallel resonance frequency f can be substantially described by using the notations in the equivalent circuit as follows:

$$f = 1/[2\pi \sqrt{\{Cp + 1/(1/Cs + 1/Cf)\}}]$$
$$= k/\sqrt{(a + b \times \epsilon)} \quad (1)$$

where k, a, and b are constants which are determined for example by the shape of the sensor such as the diameter and the thickness of the barrel-shaped insulating tube 1, the dielectric constant of the material of the barrel-shaped insulating tube 1, the distance between the conductive electrode 3 and the single-layer winding coil 4, the self-inductance of the single-layer winding coil 4.

Figure 10:
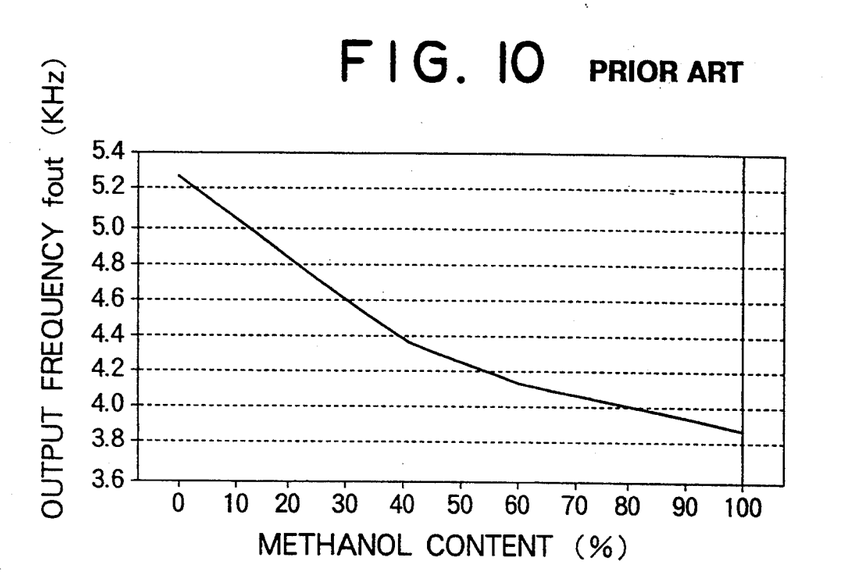
FIG. 10 is a graph illustrating the relationships between the alcohol concentration of fuel and the output frequency.

As can be seen from the equation 1, the parallel resonance frequency f depends on the dielectric constant $\epsilon$ of the fuel, therefore the parallel resonance frequency decreases with increasing dielectric constant $\epsilon$ of the fuel. For alcohol-mixed fuel containing various contents of gasoline and alcohol, the output frequency of the sensor A, that is the parallel resonance frequency f, varies according to the alcohol content (%) as shown in FIG. 10. FIG. 10 shows the case of mixed fuel containing methanol. As can be seen, the signal fout corresponding to the parallel resonance frequency f is provided from the detecting circuit B, then the dielectric constant $\epsilon$ of the alcohol-mixed fuel and thus the alcohol content (%) can be detected.

The detecting circuit B shown in FIG. 8 is configured so that the parallel resonance frequency f can be detected. The operation of this detection circuit B will be described below. In a state in which alcohol-mixed fuel is passing through the fuel path 2, the amplifier 15 provides a high frequency voltage signal to the series circuit composed of the resistor 10 and the single-layer winding coil 4. Then, the signals appearing at each end of the resistor 10, those are the high frequency voltage signal across the above-described series circuit and the high frequency voltage signal across the single-layer winding coil 4, are applied to the zero-degree phase comparator 11, which compares these signals. If, for example, a high frequency signal having a phase which is the same as that of the output frequency f of the sensor A is provided by the amplifier 15 to the above-descried series circuit comprising the resistor 10 and the single-layer winding coil 4, then the current-voltage phase of the sensor A becomes 0°. As a result, the phase difference between the high frequency voltage signals at each end of the resistor 10 becomes 0°. If, a high frequency voltage signal having a frequency lower than that of the output frequency f of the sensor A is applied to the above-described series circuit, then the current-voltage phase of the sensor A becomes ahead of 0°, and thus, the phase difference between the high frequency voltage signals at each end of the resistor 10 becomes larger than 0° as defined relative to the phase of the high frequency voltage signal applied to the above-described series circuit.

Then, the output of the zero-degree phase comparator 11 is converted by the low-pass filter 12 to a DC voltage corresponding to the phase difference. This DC voltage as well as a predetermined reference voltage Vref is input to the comparison integrator 13, which makes integration of the differences between these input signals. The output of the comparison integrator 13 is then input to the voltage-controlled oscillator 14. Thus, via the voltage-controlled oscillator 14 and the amplifier 15, the high frequency voltage signal is applied to the above-described series circuit composed of the resistor 10 and the single-layer winding coil 4. As can be seen from the above description, a phase-locked loop is formed in the detecting circuit B. In this phase-locked loop, the voltage-controlled oscillator 14 is controlled so that the phase difference between the signals appearing at each end of the above-described resistor 10 becomes 0°, that is, so that the phase difference between the voltage signal applied to the above-described series circuit and the voltage signal applied to the single-layer winding coil 4 becomes 0°. As a result, the voltage-controlled oscillator 14 always oscillates at a frequency which corresponds to the parallel resonance frequency f of the sensor A. The oscillation frequency of the voltage-controlled oscillator 14 which is in the high frequency range is divided by the frequency divider 16 down to a frequency output fout having a frequency low enough to measure the output. In this way, the dielectric constant $\epsilon$ can be determined from the frequency output fout according to equation 1, and thus the alcohol content (%) can be detected.

In the conventional apparatus fore detecting the alcohol concentration, the dielectric constant $\epsilon$ of alcohol-mixed fuel is determined from the output frequency fout of the frequency divider 16 in the detecting circuit B, based on the assumption that the dielectric constant of the alcohol-mixed fuel and the dielectric constant $\epsilon$ of the barrel-shaped insulating tube 1 do not vary. However, the actual dielectric constant $\epsilon$ of the alcohol-mixed fuel and also the actual dielectric constant of the barrel-shaped insulating tube 1 vary with change of temperature. As a result, the output frequency fout shows a significantly large change even for the constant alcohol content. Therefore, accurate detection of the alcohol content is impossible if the dielectric constant $\epsilon$ is determined simply by the output frequency fout.

SUMMARY OF THE INVENTION

It is an object of the present invention to provide an apparatus for detecting the alcohol concentration of fuel or the like, which can always provide an output frequency corresponding to the accurate alcohol content regardless of the change in temperature of the alcohol-mixed fuel. According to the present invention, an apparatus for detecting the alcohol concentration of alcohol-mixed fuel in which gasoline or light oil is mixed with an arbitrary content of alcohol comprises: dielectric constant detection means for providing a resonance frequency corresponding to the dielectric constant of alcohol-mixed fuel whose alcohol concentration is to be detected; resonance frequency detection means which detects the resonance frequency provided by the dielectric constant detection means and which outputs a first frequency output signal having a frequency which is the same as that of the resonance frequency; frequency divider with a variable dividing factor for dividing the first frequency output signal provided by the resonance frequency detection means; fuel temperature detection means which detects the temperature of the alcohol-mixed fuel and which outputs a second frequency output signal representing the detected temperature; and dividing factor decision means for determining the dividing factor of the frequency divider according to the first frequency output signal provided by the resonance frequency detection means as well as the second frequency output signal provided by the fuel temperature detection means; whereby the alcohol concentration is determined from the output frequency of the frequency divider.

In the apparatus for detecting the alcohol concentration according to the present invention, the dielectric constant of fuel is detected based on the output frequency of resonance frequency detection means, and the temperature of the fuel is detected by the fuel temperature detection means. Based on these detected results, the dividing factor decision means determines the dividing factor of the frequency divider such that the change in the output frequency due to the change in the fuel temperature may be cancelled. The frequency divider divides the frequency by the factor given by the dividing factor decision means as described above. As a result, the frequency divider can always provide an output frequency which precisely corresponds to the alcohol content regardless of the change in temperature of the fuel.

DESCRIPTION OF THE PREFERRED EMBODIMENTS

Figure 1:
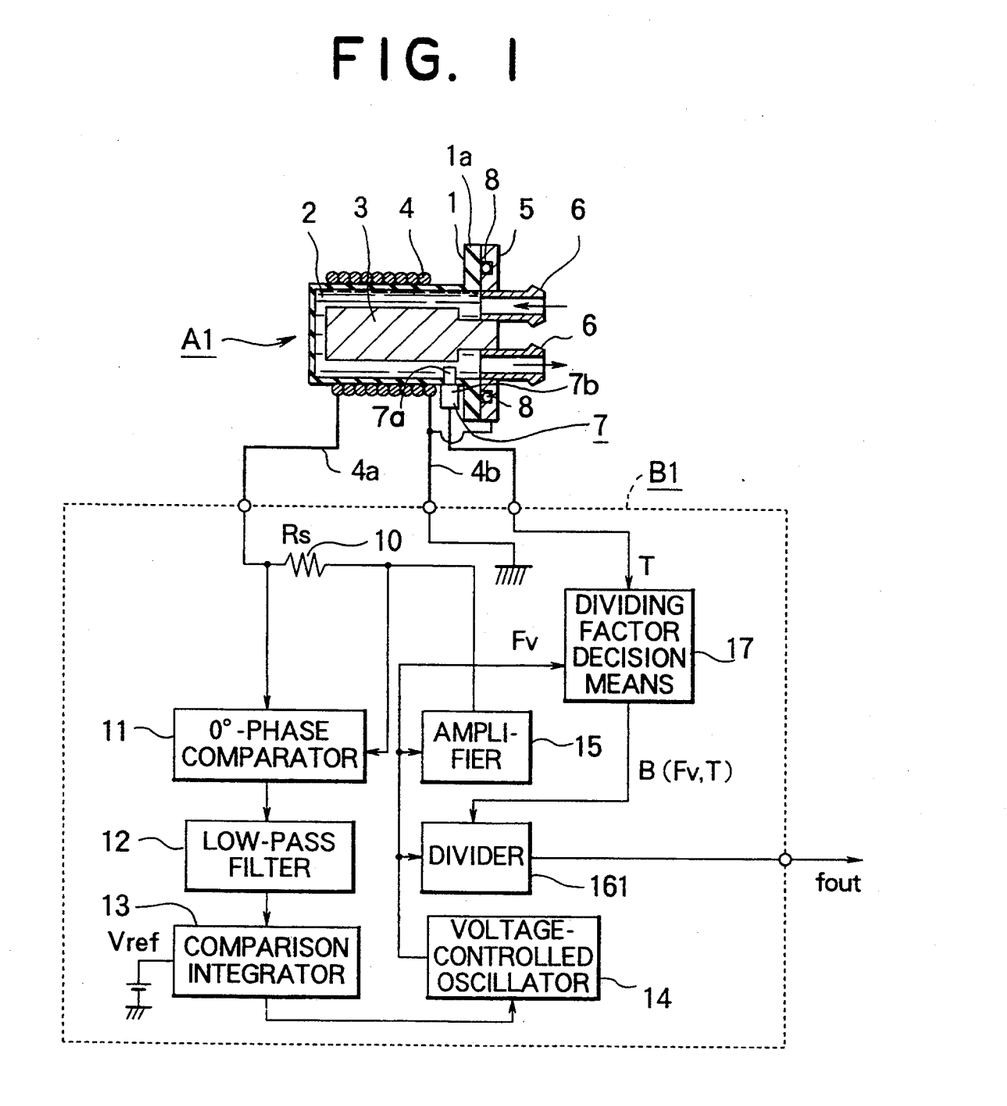
FIG. 1 is a block diagram illustrating an apparatus for detecting the alcohol concentration of alcohol-mixed fuel according to the present invention.
Figure 7:
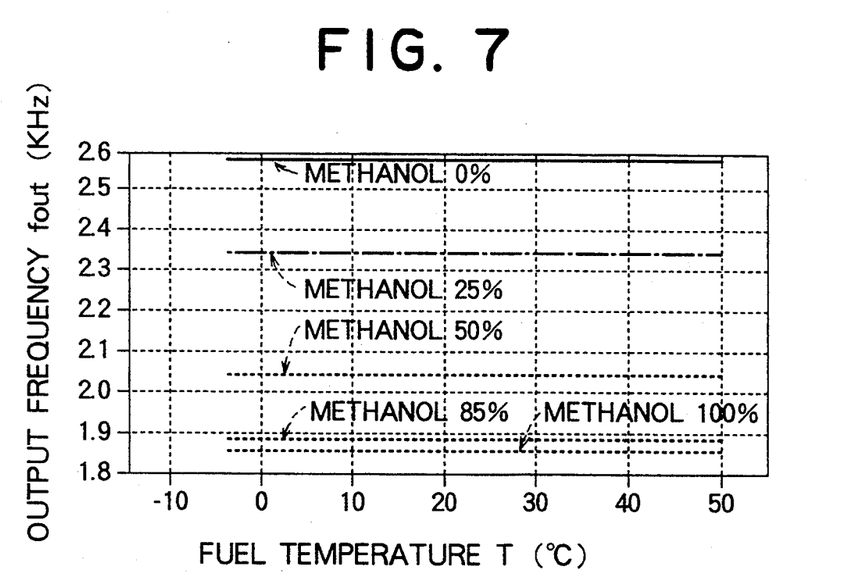
FIG. 7 is a graph illustrating the relationships between fuel temperature T and an output frequency fout according to the present invention.

Referring to the accompanying drawings, an embodiment of an apparatus for detecting the alcohol concentration of alcohol-mixed fuel containing alcohol such as methanol according to the present invention will be described below. FIG. 1 is a block diagram showing an apparatus of the present invention for detecting the alcohol concentration of alcohol-mixed fuel. In FIG. 7, a sensor A1 comprises dielectric constant detection means for providing a resonance frequency corresponding to the dielectric constant of alcohol-mixed fuel, according to this embodiment of the present invention. The sensor A1 includes a barrel-shaped insulating tube 1 made of an insulating material such as ceramic or oil-resistant plastic, wherein fuel is introduced into the barrel-shaped insulating tube 1. The sensor A1 also includes an electrically-conductive electrode 3 having a cylindrical shape coaxial to the barrel-shaped insulating tube 1 wherein the conductive electrode 3 is disposed in the barrel-shaped insulating tube 1 such that the conductive electrode 3 is substantially parallel to the barrel-shaped insulating tube 1. Preferably, the conductive electrode 3 is made of a material, which is resistant to oil such as alcohol-mixed fuel, such as titanium, stainless steel, anodized aluminum. The sensor A1 also includes a single-layer winding coil 4 wound around the barrel-shaped insulating tube 1 opposing to the conductive electrode 3 which is disposed within the barrel-shaped insulating tube 1. Both ends of the single-layer winding coil 4 are electrically connected to leads 4a and 4b, respectively. A fuel path 2 is formed between the outer surface of the conductive electrode 3 and the inner surface of the single-layer winding coil 4 via the wall of the barrel-shaped insulating tube 1 so that fuel whose alcohol concentration is to be detected can flow through the fuel path 2. The single-layer winding coil 4 is protected by the barrel-shaped insulating tube 1 from the fuel which flows through the fuel path 2.

Figure 3:
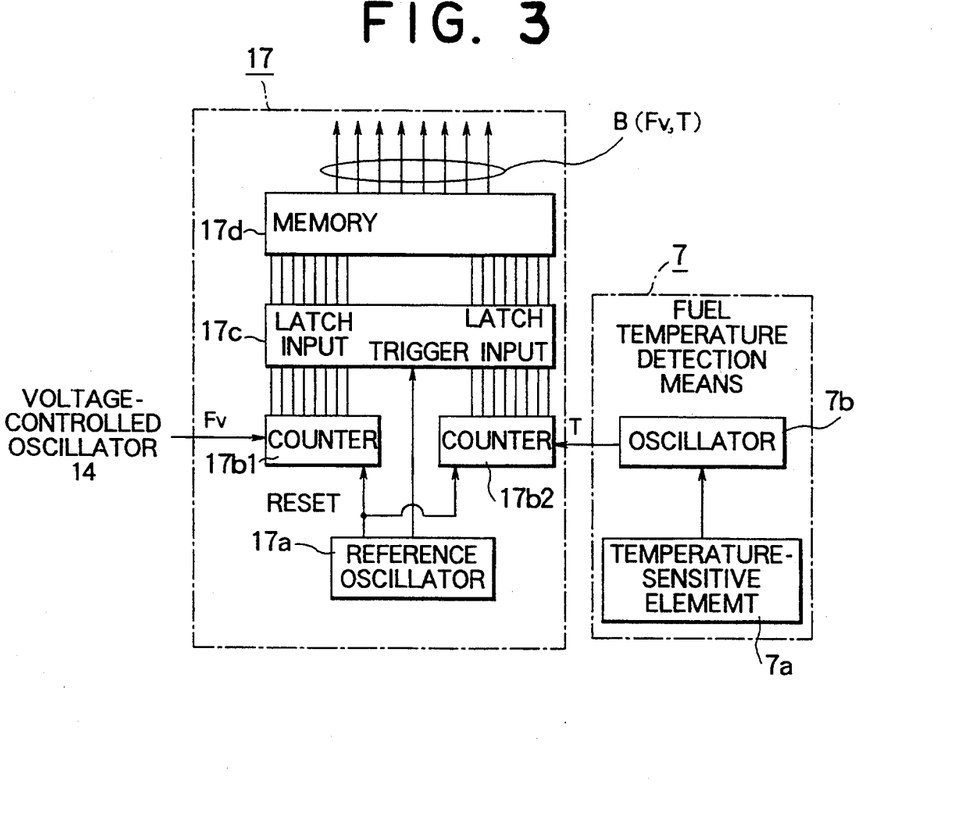
FIG. 3 is a block diagram illustrating a dividing factor decision means according to the present invention.

The conductive electrode 3 is also provided at its open end with a flange 5 which is fixed via a fuel seal 8 to the barrel-shaped insulating tube 1 in such a manner that the whole of these elements form a fuel chamber. The flange 5 may be formed as an integral part of the conductive electrode 3, as shown in FIG. 1. A pair of nipples 6 are provided through the flange 5 so that the fuel may be introduced into the fuel path 2. According to the present invention, the apparatus for detecting the alcohol concentration also has fuel temperature detection means 7 for detecting the temperature of fuel filled in the fuel path 2. As shown in FIG. 3, the fuel temperature detection means 7 comprises a temperature-sensitive element 7a such as a thermistor whose resistance varies according to the fuel temperature detected and a signal generator 7b for providing a pulse signal having a frequency corresponding to the resistance of the temperature-sensitive element 7a.

The detecting circuit B1 in this embodiment will be described below. As shown in FIG. 1, the detecting circuit B1 comprises a resistor 10 electrically connected to the lead 4a of the single-layer winding coil 4 in such a manner that a series circuit is formed with the resistor 10 and the single-layer winding coil 4. Each end of the resistor 10 is electrically connected to a zero-degree phase comparator 11 so that a voltage signal across the series circuit comprising the resistor 10 and the single-layer winding coil 4 and a voltage signal across the single-layer winding coil 4 are applied to the zero-degree phase comparator 11. The detecting circuit B1 further comprises a low-pass filter 12 to which the output of the zero-degree phase comparator 11 is applied; a comparison integrator 13 to which the output of the low-pass filter 12 as well as a predetermined reference voltage Vref corresponding to the phase of 0° is applied; a voltage-controlled oscillator 14 to which the output of the comparison integrator 13 is applied; and an amplifier 15 which amplifies the output of the voltage-controlled oscillator 14 and provides the amplified high frequency signal to the series circuit comprising the resistor 10 and the single-layer winding coil 4. In this way, a resonance frequency detection means is composed of the zero-degree phase comparator 11, the low-pass filter 12, the comparison integrator 13, the voltage-controlled oscillator 14, and the amplifier 15 such that the resonance frequency detection means outputs a frequency output signal having a frequency which is the same as the resonance frequency provided by the sensor A1 acting as the dielectric constant detection means. In the present invention, the detecting circuit B1 also comprises dividing factor decision means 17 for determines the frequency dividing factor from the frequency of the output signal of the voltage-controlled oscillator 14 and the output signal of the fuel temperature detection means 7 so that the change of the output frequency of a frequency divider 161 due to the change of temperature is cancelled. The detecting circuit B1 also comprises a frequency divider 161 electrically connected to the dividing factor decision means 17 for dividing the output frequency of the voltage-controlled oscillator 14 by the variable dividing factor determined by the dividing factor decision means 17.

In the conventional technique described above referring to FIG. 8, since the frequency divider 16 divides the output frequency of the voltage-controlled oscillator 14 by a fixed dividing factor, a significantly large change in the output frequency fout occurs due to the change in temperature of fuel, which makes impossible to achieve accurate detection. In contrast, in the present invention, the variable frequency dividing factor is determined responding to the change in temperature of fuel so that the output frequency becomes independent of the change in temperature of the fuel. Based on the dividing factor, the frequency divider 161 performs the dividing operation. As a result, no change of the output frequency occurs even if the fuel temperature changes, as shown in FIG. 7, thereby a very accurate detection can be achieved.

Figure 11:
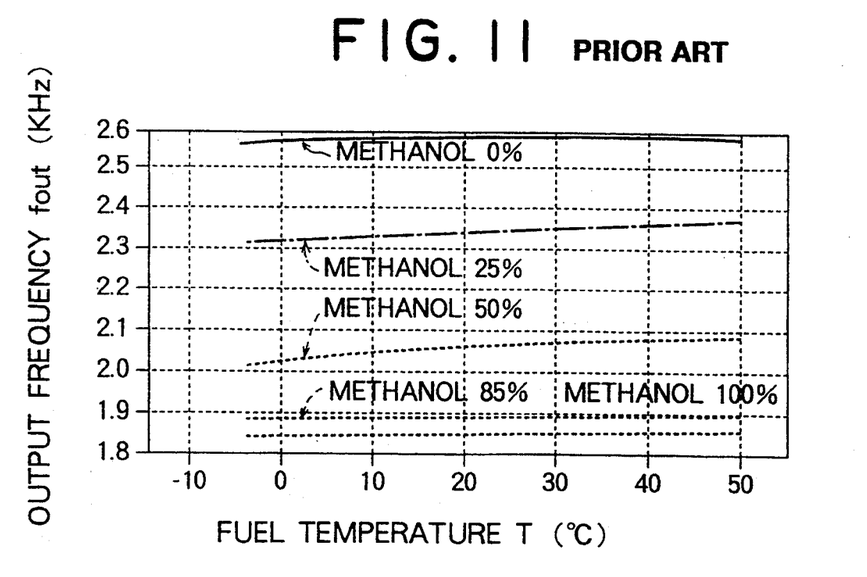
FIG. 11 is a graph illustrating the relationships between fuel temperature T and the output frequency fout according to the conventional apparatus.

A method of determining the frequency dividing factor will be described below. It will be assumed that the output frequency fout of the frequency divider 16 according to the convention technique shown in FIG. 8 can be represented by a functional equation f(R,T), where R is the alcohol content and T is the temperature of fuel. It will be also assumed that the reference output frequency for the alcohol content R can be represented by F(R). That is, the graphical representation of f(R,T) corresponds to FIG. 11, and the graphical representation of F(R) corresponds to FIG. 7. The output frequency Fv of the voltage-controlled oscillator 14 can be described by the following equation (2):

$$Fv = 2048 \times f(R, T) \quad (2)$$

Therefore, if the frequency dividing factor B(Fv, T) of the frequency divider 161 according to the present invention is determined such that the following equation (3) is met, then the output frequency of the frequency divider 161 becomes F(R) which no longer depends on temperature.

$$B(Fv, T) = F(R)/Fv \quad (3)$$

Figure 2:
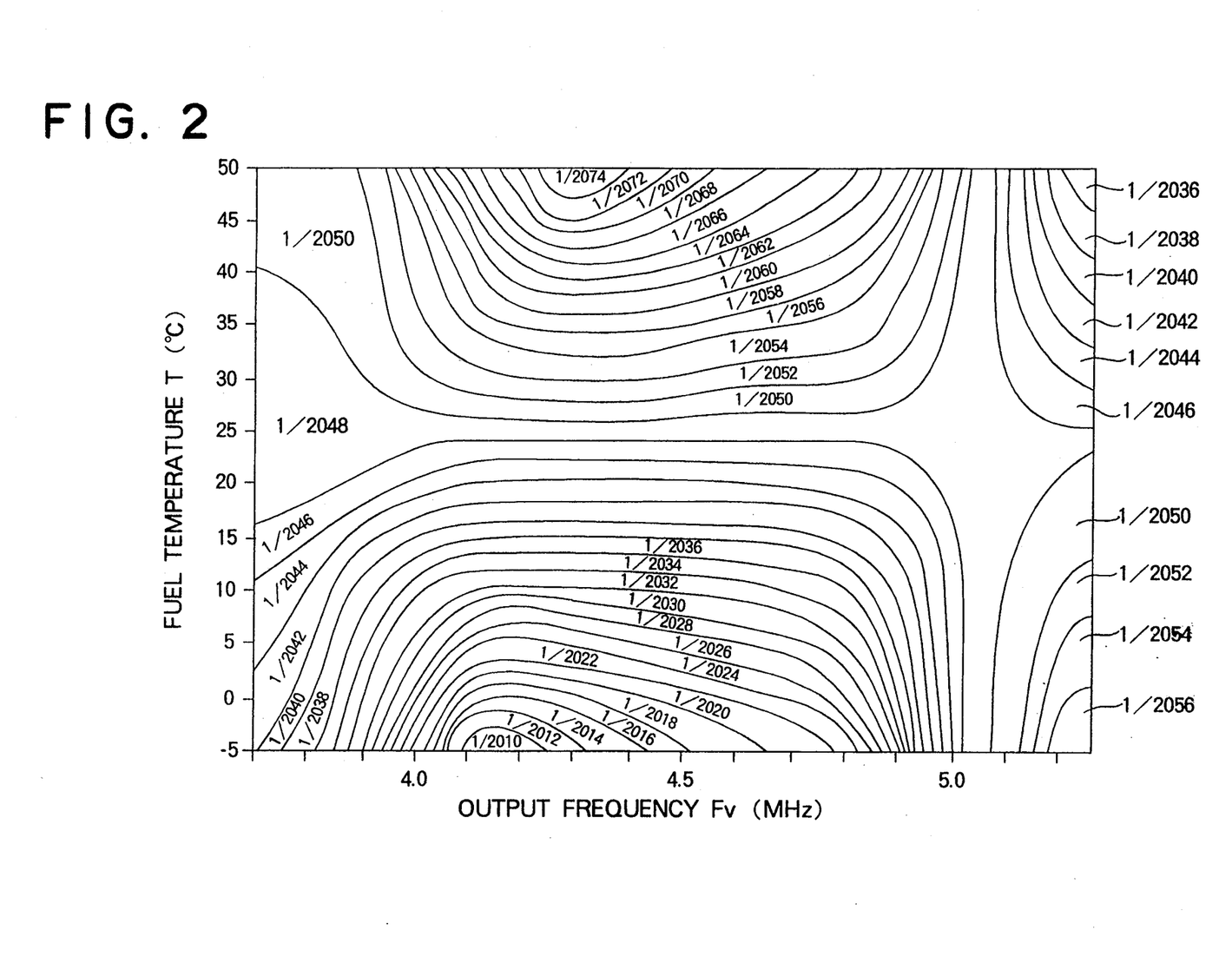
FIG. 2 is a map illustrating the relationships among a frequency dividing factor of a frequency divider, an output frequency Fv and fuel temperature T.

FIG. 2 is a contour map which graphically represents B(Fv, T). The dividing factor decision means 17 determines the frequency dividing factor B from the output frequency Fv provided by the voltage-controlled oscillator 14 and the output T provided by the fuel temperature detection means 7 by using the map shown in FIG. 2. Then, the frequency divider 161 divides the output frequency of the voltage-controlled oscillator 14 by the determined dividing factor B so as to provide an appropriate frequency. As a result, constant output performances as shown in FIG. 7 can always be obtained independent of the temperature of fuel.

Figure 4:
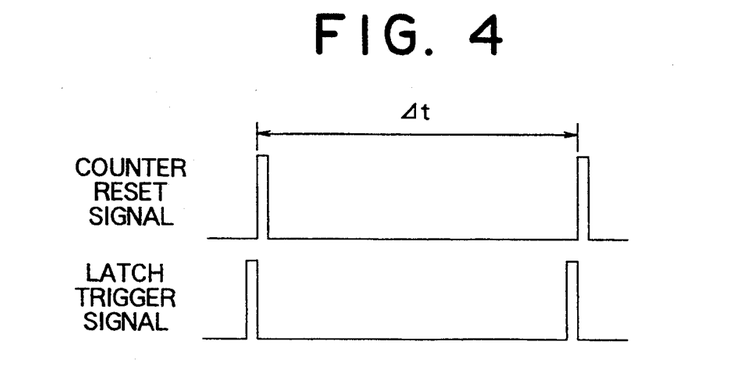
FIG. 4 is a timing chart associated with a reset signal of a counter and a latch trigger signal.

An embodiment of the dividing factor decision means 17 will be described below referring to FIG. 3. The dividing factor decision means 17 comprises a reference oscillator 17a which outputs a counter reset signal and a latch trigger signal at predetermined periodic time intervals $\Delta t$ as shown in FIG. 4; a counter 17b1 which counts a pulse signal Fv representing the output frequency provided by the voltage-controlled oscillator 14 (FIG. 1) and which outputs a resultant frequency count signal; a counter 17b2 which counts a pulse signal T representing the fuel temperature provided by the above-described fuel temperature detection means 7 and which outputs a resultant temperature count signal; a latch circuit 17c for holding the frequency count signal and the temperature count signal provided by the counters 17b1 and 17b2, respectively; and memory 17d which can be addressed by the output of the latch circuit 17c. The memory 17d stores data associated with the frequency dividing factors B(Fv, T) as a function of the output frequency Fv provided by the voltage-controlled oscillator 14 and the fuel temperature T provided by the fuel temperature detection means 7. The data stored in the memory 17d is provided to the frequency divider 161 (FIG. 1).

As shown in FIG. 3, after the two counters 17b1 and 17b2 are cleared to 0 by the counter reset signal provided by the reference oscillator 17a, these counters 17b1 and 17b2 perform counting up for a time period $\Delta t$ and then output the frequency count signal and the temperature count signal, respectively. Then, responding to the latch trigger signal from the reference oscillator 17a, the latch circuit 17c latches the outputs counted up by the counters 17b1 and 17b2 for a time period $\Delta t$ to supplies the outputs to the memory 17d. The counters 17b1 and 17b2 are again cleared to 0 by the next counter reset signal provided by the reference oscillator 17a and start counting up. However, the outputs of the latch circuit 17c are not cleared, and thus the previous counted up results will be held for the time period $\Delta t$ until the completion of the following counting up operation. In other words, the outputs of the latch circuit 17c are updated each time period $\Delta t$.

The outputs of the counters 17b1 and 17b2 represent the counting up results which are obtained by counting up the output frequency Fv provided by the voltage-controlled oscillator 14 and the fuel temperature output T provided by the fuel temperature detection means 7, respectively, for a predetermined time period $\Delta t$. Therefore, if the memory 17d is accessed by specifying a lower address by the output of the counter 17b1 and a upper address by the output of the counter 17b2, then it is possible to refer to the map such that as shown in FIG. 2 so as to provide a required frequency dividing factor B as an output via the output of the memory 17d.

Figure 5:
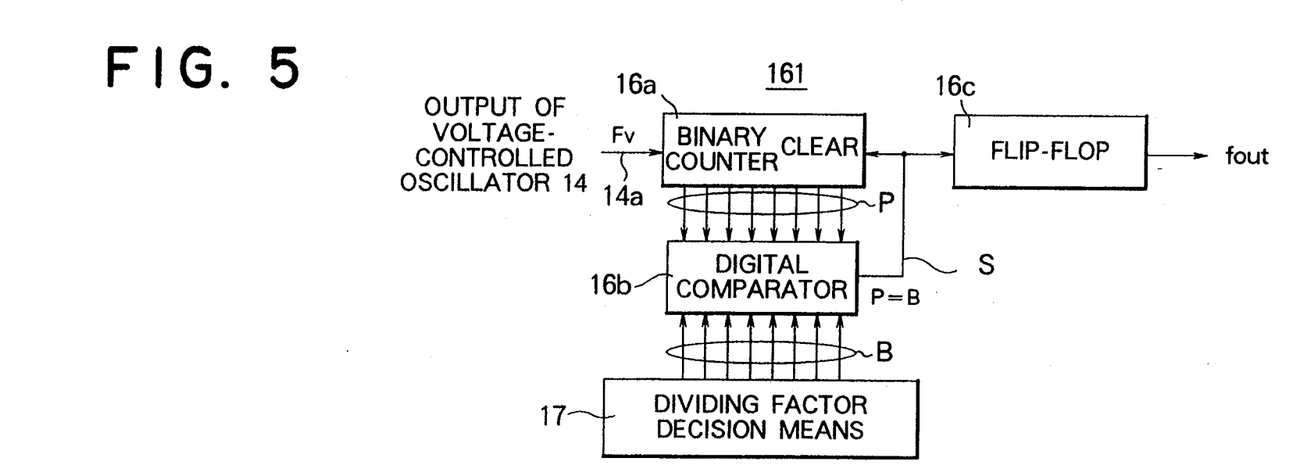
FIG. 5 is a block diagram illustrating a frequency divider according to the present invention.
Figure 6:
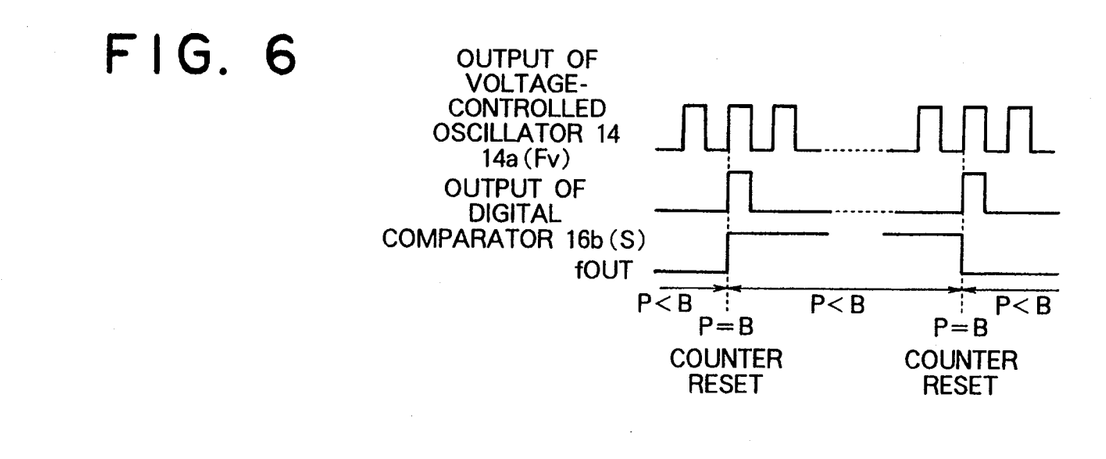
FIG. 6 is a timing chart illustrating the relationships between output signals of the frequency divider shown in FIG. 5.

FIG. 5 shows an embodiment of a frequency divider 161 in which the frequency dividing factor B can be changed by the above-described output of the dividing factor decision means 17. In FIG. 5, reference numeral 74a denotes an output Fv provided by the voltage-controlled oscillator 14, wherein the output Fv corresponds to the resonance frequency of the sensor A1. As shown in FIG. 5, the frequency divider 161 comprises a binary counter 16a which counts up the output 14a of the voltage-controlled oscillator 14 so as to provide a bit output P; and a digital comparator 16b to which the bit output P of the binary counter 16a and the bit output B of the dividing factor decision means 17 are applied. The digital comparator 16b has three ports, P-port, B-port and "P=B"-port (not shown). The P-port and B-port are applied with the bit output P of the binary counter 16a and the bit output B of the dividing factor decision means 17, respectively, so as to make comparison between these bit outputs P and B. If P=B, then an EQUAL signal S is output from the "P=B"-port (not shown). In FIG. 5, there is also shown a flip-flop 16c which inverts its output each time an EQUAL signal S is applied thereto.

The operation of this frequency divider will be described below. The binary counter 16a performs the counting up operation responding to the rising or falling timing of the output 14a of the voltage-controlled oscillator 14. The counted value is provided as the bit output P in a digital form to the P-port of the digital comparator 16b. On the other hand, the bit output B of the dividing factor decision means 17 is applied to the B-port of the digital comparator 16b. The digital comparator 16b compares P with B. If P=B, then the EQUAL signal S at the "P=B"-port rises. This EQUAL signal S is applied to the CLEAR port of the binary counter 16a, so as to reset the binary counter 16a. Then, the condition P<B will be met, and thus the EQUAL signal S will go down.

The EQUAL signal S which represents P=B is also applied by the digital comparator 16b to the flip-flop 16c, thereby inverting the output signal fout of the flip-flop 16c. That is, the EQUAL signal S which represents P=B provides a pulse signal each time the binary counter 16a completes the counting up of the output 14a of the voltage-controlled oscillator 14 from 0 to the value B set by the dividing factor decision means 17.

On the other hand, since the output signal fout of the flip-flop 16c is inverted each time the EQUAL signal S indicating P=B is applied by the digital comparator 16b, the cyclic time period of the output signal fout corresponds to 2×B as long as outputs 14a of the voltage-controlled oscillator 14. This means that the output fout of the flip-flop 16c is determined by the output B of the dividing factor decision means 17 in such a manner that the output signal fout of the flip-flop 16c provides a frequency which is obtained by dividing the output 14a of the voltage-controlled oscillator 14 down to 1/(2×B).

In the embodiment described above, the single-layer winding coil 4 of the sensor A1 and the conductive electrode 3 are coaxial to each other. However, the present invention is not limited to such a coaxial structure. Any structure may also be used for the same purpose as long as the structure can provide capacitance associated with fuel which resides between the conductive electrode 3 and the circumferential face of the single-layer winding coil 4.

In the above-described embodiment according to the present invention, the apparatus for detecting the alcohol concentration is used for detecting the alcohol content of alcohol-mixed fuel containing alcohol such as methanol. However, the apparatus of the present invention may also be applied to the alcohol content detection for a wide variety of liquid.

As described above, the present invention provides an apparatus comprising fuel temperature detection means 7 for detecting the temperature of alcohol-mixed fuel in which gasoline or light oil is mixed with an arbitrary content of alcohol; and dividing factor decision means 17 for determining the frequency dividing factor according to the resonance frequency Fv detected by a resonance frequency detecting means and the change in temperature of the alcohol-mixed fuel detected by the fuel temperature detection means 7; whereby the resonance frequency Fv is divided by the frequency dividing factor determined by the dividing factor decision means 17 so that accurate detection of the alcohol content may always be achieved regardless of the change in temperature of the fuel.

What is claimed is:

1. An apparatus for detecting the concentration of alcohol in a mixed fuel in which an arbitrary content of alcohol is mixed with gasoline or tight oil, said apparatus comprising:

dielectric constant detection means for providing a resonance frequency corresponding to the dielectric constant of alcohol-mixed fuel whose alcohol concentration is to be detected;

resonance frequency detection means which detects said resonance frequency provided by said dielectric constant detection means so as to provide a first frequency output signal having the same frequency as said resonance frequency;

a frequency divider which divides said first frequency output signal provided by said resonance frequency detection means by a variable frequency dividing factor;

fuel temperature detection means which detects the temperature of said alcohol-mixed fuel so as to provide a second frequency output signal representing said temperature; and dividing factor decision means for determining said frequency dividing factor based on said first frequency output signal provided by said resonance frequency detection means and said second frequency output signal provided by said fuel temperature detection means;

wherein the alcohol concentration is determined by the output frequency of said frequency divider.

2. An apparatus for detecting the concentration of alcohol as claimed in claim 1, wherein said dividing factor decision means comprises:

a reference oscillator for outputting a counter reset signal and a latch trigger signal at each predetermined timing;

a first counter which counts said first frequency output signal provided by said resonance frequency detection means for a time period determined by said predetermined timing according to said counter reset signal provided by said reference oscillator to output a frequency count signal;

a second counter which counts said second frequency output signal provided by said fuel temperature detection means for a time period determined by said predetermined timing according to said counter reset signal provided by said reference oscillator to output a temperature count signal;

a latch circuit which responds to the latch trigger signal provided by said reference oscillator to hold said frequency count signal and said temperature count signal provided by said first and second counters, respectively, for a time period determined by said predetermined timing; and memory which stores data associated with the frequency dividing factors, said data being stored at locations having addresses corresponding to each of said frequency count signal and each of said temperature count signal, wherein said data associated with the frequency dividing factor is accessed by the addresses corresponding to said frequency count signal and said temperature count signal provided by said latch circuit.

3. An apparatus for detecting the concentration of alcohol as claimed in claim 1, wherein said frequency divider comprises:

a binary counter which counts said first frequency output signal provided by said resonance frequency detection means to output a signal;

a digital comparator which receives the data associated with the frequency dividing factor provided by said dividing factor decision means and said signal provided by said binary counter, and which compares said signal with said data associated with the frequency dividing factor to output an equal-signal when said signal is equal to said data associated with the frequency dividing factor;

said binary counter being reset each time when said equal-signal is input from said digital comparator; and a flip-flop which inverts its output each time when said equal-signal is input from said digital comparator;

whereby said concentration of alcohol of alcohol-mixed fuel is detected from the output of said flip-flop.

4. An apparatus for detecting the concentration of alcohol as claimed in claim 2, wherein said frequency divider comprises:

a binary counter which counts said first frequency output signal provided by said resonance frequency detection means to output a signal;

a digital comparator which receives the data associated with the frequency dividing factor provided by said dividing factor decision means and said signal provided by said binary counter, and which compares said signal with said data associated with the frequency dividing factor to output an equal-signal when said signal is equal to said data associated with the frequency dividing factor;

said binary counter being reset each time when said equal-signal is input from said digital comparator; and a flip-flop which inverts its output each time when said equal-signal is input from said digital comparator;

whereby said concentration of alcohol of alcohol-mixed fuel is detected from the output of said flip-flop.

* * * * *